United States Patent [19]

Castagnola et al.

[11] Patent Number: 4,892,868
[45] Date of Patent: Jan. 9, 1990

[54] DERIVATIVES OF BILIARY ACIDS, PROCESS FOR THE PRODUCTION THEREOF AND CORRESPONDING PHARMACEUTICAL COMPOSITIONS

[75] Inventors: Virginio Castagnola, Milan; E. Giuliano Frigerio, Bresso; Roberto Pellicciari, Perugia; Aldo Roda, Bologna, all of Italy

[73] Assignee: Gipharmex, S.p.A., Milan, Italy

[21] Appl. No.: 884,003

[22] Filed: Jul. 10, 1986

Related U.S. Application Data

[63] Continuation-in-part of Ser. No. 641,741, Aug. 17, 1984, abandoned.

[51] Int. Cl.$^4$ ............... A61K 31/575; C07J 9/00
[52] U.S. Cl. .................... 514/182; 514/877; 260/397.1
[58] Field of Search ............ 260/397.1; 514/177, 514/178, 182, 877

[56] References Cited

U.S. PATENT DOCUMENTS

| | | | |
|---|---|---|---|
| 4,104,285 | 8/1978 | Gallo-Torres et al. | 260/397.1 |
| 4,117,121 | 9/1978 | Gallo-Torres et al. | 260/397.1 |
| 4,425,273 | 1/1984 | Iida et al. | 260/397.1 |
| 4,440,688 | 4/1984 | Scolastico et al. | 260/397.1 |
| 4,514,393 | 4/1985 | Castagnola et al. | 260/397.1 |
| 4,565,810 | 1/1986 | Castagnola et al. | 260/397.1 |
| 4,565,811 | 1/1986 | Di Schiena | 260/397.1 |
| 4,648,995 | 3/1987 | Mosbach et al. | 260/397.1 |
| 4,681,876 | 7/1987 | Marples et al. | 260/397.1 |

FOREIGN PATENT DOCUMENTS

| | | | |
|---|---|---|---|
| 0101554 | 2/1984 | European Pat. Off. | |
| 232788 | 8/1987 | European Pat. Off. | 260/397.1 |
| 259185 | 3/1988 | European Pat. Off. | 260/397.1 |
| 3623747 | 1/1988 | Fed. Rep. of Germany | 260/397.1 |
| 250538 | 10/1987 | German Democratic Rep. | 260/397.1 |
| 6039100 | 4/1981 | Japan | 260/397.1 |
| 161996 | 8/1985 | Japan | 260/397.1 |
| 2198698 | 9/1987 | Japan | 260/397.1 |
| 2076823 | 12/1981 | United Kingdom | 260/397.1 |

OTHER PUBLICATIONS

Fetizon et al., Chem. Abst. 82-112198v (1975) "Convenient new procedure for the oxidative cleavage . . . ".
Sawaya et al., Chem. Abst. 100-139458g (1984) "Metal ion-catalyzed oxidation of steroids: XXI".
Pellicciari et al, J. Med. Chem. 1984, 27, pp. 746-749.
Seifert et al, JACS, vol. 94 (1972) pp. 5880-5887.
Gottarelli et al, Chem. Abst. 67-82301u (1967) "Optical rotatory dispersion XLVII . . . ".
Seifert et al, Chem. Abst. 75-153504r (1971) "First identification of steroid carboxylic acid in petroleum".

*Primary Examiner*—Cecilia Shen
*Attorney, Agent, or Firm*—Birch, Stewart, Kolasch & Birch

[57] ABSTRACT

New derivatives of chenodeoxycholic, ursodeoxycholic, cholic and ursocholic acids, bearing a methyl group in the side chain, in an alfa position to the carboxylic group, the corresponding nor- and di-nor- derivatives, and the corresponding conjugates with taurine and glycine, are described.

The compounds of the invention are prepared by methylation of the esters with methyl iodide in the presence of lithium-dialkylamides.

15 Claims, No Drawings

DERIVATIVES OF BILIARY ACIDS, PROCESS FOR THE PRODUCTION THEREOF AND CORRESPONDING PHARMACEUTICAL COMPOSITIONS

This application is a continuation-in-part of Ser. No. 06/641,741 filed on Aug. 17, 1984, now is abandoned.

The present invention relates to new derivatives of biliary acids of formula I $$St-\underset{R_1}{\underset{|}{\overset{CH_3}{\overset{|}{C}}}}-\left[(CH_2)_m-\underset{}{\overset{CH_3}{\overset{|}{CH}}}\right]_n-COX \quad (I)$$

wherein:
St represents the 17-ethiocholanyl residue, having two or more hydroxy groups both in the $\alpha$ and $\beta$ conformation, some of which being optionally replaced by keto groups;
m and n are zero or 1;
when n is 1, $R_1$ is hydrogen, whereas when n is zero, $R_1$ is methyl;
X represents OH, $OR_3$ (where $R_3$ is a pharmaceutically acceptable cation) or taurine and glycine residues, optionally salified, of formula $-NH(CH_2)_2SO_3H$ and $-NH-CH_2-COOH$;
and to all the possible stereoisomers thereof.

The compounds of formula I present valuable pharmacological properties which make them useful for treating various disorders of the hepatobiliary function, with particular reference to cholesterol metabolism and bile production. Experiments with laboratory animals and clinical trials as well show a choleretic activity which is especially marked with those compounds which are not conjugated with taurine or glycine. These compounds, hence, can be used for treating conditions of cholestasis and for general regulation of the cholesterol metabolism. The taurine or glycine conjugated compounds are easily eliminated with bile and they have an outstanding stability against degradation as usually effected by the bacteria of intestinal flora. Owing to these properties, they are useful for treating cholesterol gallstones, thus providing an alternative to the conventional treatment with ursodeoxycholic acid at even much lower effective dosage.

Quite generally, the new compounds prove therapeutically active at a dosage level which is substantially lower than with the compounds hitherto conventionally used. Usually, amounts of from 250 to 500 mg a day are effective if daily administration is secured for the whole treatment duration which as a rule is very long, especially in the case of cholesterol gallstones. The compounds are advantageously administered as capsules or tablets to be ingested orally, preferably with the meals.

Comparative trials have been carried out, using as a reference compound ursodeoxycholic acid (UDCA) which is the most commonly used medicine in the treatment of cholesterol gallstones; the compound of Example 1, i.e. the 23-methyl derivative of ursodeoxycholic acid (hereinafter referred to as MUDCA), was chosen as a typical representative of the new compounds. The test methods are well known in the art; they are described, for instance, in J. Med. Chem. 27 (1984), 746-749.

As a result, there has been shown that the 23-methyl derivative (MUDCA) has a substantially higher critical micellar concentration than UDCA, the value thereof being 28 mmole versus 19 mmole with UDCA.

In the evaluation for natural degradation by incubating with human faeces for 24 hours, MUDCA has proved to remain unaltered at completion of the test whereas UDCA underwent a substantially quantitative degradation to lithocholic acid within as short an incubation time as 1 to 2 hours.

The choleretic activity, i.e. the bile flow increasing action, of MUDCA again is unexpectedly higher than that of UDCA: in rats, it amounts to 64 $\mu l/\mu mole$ as compared to 16 $\mu l/\mu mole$ with UDCA.

Furthermore, the hepatic tolerance also is much more elevated with the new compound, particularly at higher dosage and with animal species which are known to be more sensitive as are, inter alia, rabbits. Administering to rabbits 50 and 200 mg/kg/day, respectively, of MUDCA for three months did not result in any damaging effect, while UDCA usually causes clinical and histopathological alterations in the course of treatment.

Summarizing now, the new compounds as compared with ursodeoxycholic acid show significantly improved properties as regards cholesterol-dissolving ability and stimulation of the bile flow. Moreover, these properties are added with an exceptional stability against natural degradation and a remarkable hepatic tolerance. This pharmacological spectrum outstandingly enables the compounds according to the invention for a long term treatment of the above mentioned therapeutical indications.

Such a favorable combination of properties, however, was quite unexpected, especially when considering the close structural relation of the new compounds and the bile acids.

The invention refers also to pharmaceutical compositions containing as the active principle one or more compounds of formula (I).

Non-limiting examples of compounds (I) of the present invention include:
Sodium tauro-3$\alpha$,7$\beta$-dihydroxy-23-methyl-5$\beta$-cholanate;
3$\alpha$,7$\beta$-dihydroxy-23-dimethyl-5$\beta$-cholanoic acid;
glyco-3$\alpha$,7$\alpha$-dihydroxy-23-nor-22-methyl-5$\beta$-cholanoic acid;
3$\alpha$,7$\beta$,12$\alpha$-trihydroxy-23-nor-22-dimethyl-5$\beta$-cholanoic acid;
3$\alpha$,7$\beta$-dihydroxy-23-methyl-5$\beta$-cholanoic acid;
sodium 3$\alpha$,7$\beta$-dihydroxy-23-methyl-5$\beta$-cholanate;
3$\alpha$,7$\alpha$-dihydroxy-23-methyl-5$\beta$-cholanoic acid;
3$\alpha$,7$\alpha$-dihydroxy-23-dimethyl-5$\beta$-cholanoic acid;
3$\alpha$,7$\alpha$,12$\alpha$-trihydroxy-21,22,23-tris-nor-20-dimethyl-5$\beta$-cholanoic acid;
sodium tauro-3$\alpha$-hydroxy-7-keto-23-methyl-5$\beta$-cholanate;
3$\alpha$,7$\alpha$-dihydroxy-22-methyl-24-nor-5$\beta$-cholanoic acid;
3$\alpha$,7$\alpha$,12$\alpha$-trihydroxy-22-methyl-24-nor-5$\beta$-cholanoic acid.

The compounds (I) conjugated with taurine or glycine are prepared from the corresponding acids (X=OH) by reaction with taurine or glycine in the presence of N-ethoxycarbonyl-2-ethoxy-1,2-dihydroquinoline (EEDQ), in alcoholic or hydroalcoholic solution.

Glycine or taurine are generally added to the reaction mixture in aqueous alkali hydroxide solution.

The reaction can be carried out at temperatures ranging between room temperature and the reflux temperature of the solvent, preferably between 30° and 50° C.

Compounds (I) are prepared from cholanic, nor-cholanic or di-nor-cholanic acids, by means of a series of reactions that provide protection of the hydroxylic groups on the 17-ethiocholanyl moiety and of the carboxylic group; methylation in α to the protected carboxylic group with methyl iodide and lithium-dialkylamides, elimination of the protective groups and, optionally, salification or conjugation.

Hydroxy groups can be properly protected by acetylation, whereas the carboxy group is suitably converted into the methyl or ethyl ester.

The methylation reaction requires strictly anhydrous conditions, the use of aprotic solvents such as tetrahydrofuran, or 1,2-dimetoxyethane, temperatures between −18° C. and −25° C., absence of air or oxygen, and the use of lithium cyclohexylisopropylamide or lithium-dicyclohexylamide. Possible mixtures of mono- and dimethylated compounds can be separated with conventional chromatographic techniques, as conventional are the cleavage of the protective groups and the optional salification. The conjugation, on the contrary, is carried out as already described.

The starting product may be natural biliary acids or their nor-derivatives, that can be obtained through degradation reactions of the chain.

Of course it is possible to make many changes in the above-mentioned method, without departing, however, from the scope of the invention: for example, phase-transfer techniques can be used, as well as different protection-methods of the hydroxy groups of the St nucleus, of the carboxy group, etc.

It is also obvious that the products obtained from the above described processes can be present in numerous isomeric forms from the steric point of view.

The invention refers of course to all the possible stereoisomers of the claimed compounds.

The following examples further illustrate the process of the invention, without limiting in any way the scope thereof.

EXAMPLE 1

(a)
3α,7β-diethoxycarbonyl-23-methyl-5β-cholan-24-oic acid, methyl ester n-Butyllithium (24 ml, 1.6 moles) was added during 20 minutes to a solution of isopropylcyclohexylamine (8 ml) in anhydrous tetrahydrofuran (30 ml), under stirring and in nitrogen atmosphere. Ten minutes after the addition, the solution was cooled to −78° C. and the methyl ester of 3α,7β-diethoxycarbonyl-5β-cholanoic acid (4.7 g) dissolved in tetrahydrofuran (25 ml) was slowly added. After 15 minutes, methyl iodide (21.6 g) was slowly added; after the addition, the mixture was allowed to raise to room temperature and was stirred for 16 hours. The reaction mixture was poured in water (100 ml) and extracted with chloroform (3×20 ml). The collected organic phases were washed with hydrochloric acid (3×15 ml, 0.1N) and with NaCl-saturated water (2×20 ml).

After drying on anhydrous Na$_2$SO$_4$, and evaporation of the solvent, 6.5 g of raw product are obtained, that is subsequently eluted in a silica gel column with petroleum ether/ethylether 9/1. 3.5 Grams of product (72%) are obtained. IR (Nujol), cm$^{-1}$: 1730 (C=O).

NMR (CDCl$_3$), δ: 0.67 (s, 3H, 18—CH$_3$); 0.96 (s, 3H, 19—CH$_3$); 1.13 (d, 2H, 23α—+23β—CH$_3$); 2.0 (d, 6H, 3—CH$_3$—CO and 7—CH$_3$CO); 3.6 (d, 3H, COOCH$_3$); 4.67 (br$_4$m, 2H, 3β—CH and 7α—CH).

(b) 3α,7β-Dihydroxy-23-methyl-5β-cholan-24-oic acid

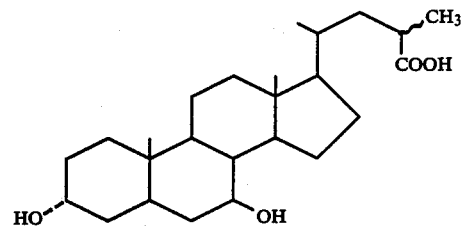

A solution of the methyl ester of 3α,7β-diethoxycarbonyl-23-methyl-5β-cholanoic acid (1 g) in KOH/MeOH (100 ml, 10%) was refluxed under stirring for 24 hours. The reaction mixture was subsequently poured into water (150 ml), extracted with diethyl ether (2×30 ml), acidified with hydrochloric acid (10%) and extracted with ethyl acetate (3×30 ml). The collected ethyl acetate extracts were washed with NaCl saturated water, dried on anhydrous Na$_2$SO$_4$, and the solvent was evaporated under vacuum. The obtained raw product (1 g) was eluted in a silica gel column with petroleum ether/ethyl acetate 8/2; 300 mg of pure product (40%) were thus obtained, m.p. 125°–127° C.

Ir (Nujol), cm$^{-1}$: 3580–3210 (OH); 3110–2780 (CH$_3$, CH$_2$); 1720 (CO); 1470 (CH$_2$); 1050 (CO).

NMR (CD$_3$OD), δ: 0.70 (s, 3H, 18—CH$_3$); 0.93 (s, 3H, 19—CH$_3$); 1.03–1.16 (d, 3H, 23α—+23β—CH$_3$); 3.23–3.66 (br m, 2H, 3β—CH and 7α—CH); 4.80 (m, 3H, 3α—OH, 7β—OH and 24 COOH).

Mass (M/e$^-$) M$^+$: 406.

(c) 3α,7β-Dihydroxy-23α-methyl-5β-cholan-24-oic acid and
3α,7β-dihydroxy-23β-methyl-5β-cholan-24-oic acid 1.22 Grams of the compound obtained as described in (b) were eluted on a silica column using chloroform/methanol 95/5 as eluent. A first fraction of 240 mg was obtained (A-isomer), then a second one of 800 mg (a mixture of A- and B-isomer), then a last fraction of 120 mg of B-isomer. The A-isomer (a white pulver) melts at 210° C., and it is soluble in methanol, ethanol, acetone. It was identified as 23α-methyl-ursodeoxycholic acid (=3α,7β-dihydroxy-23α-methyl-5β-cholan-24-oic acid) through the IR and NMR spectra:

IR (Nujol), cm$^{-1}$: 3580–3210 (OH); 3110–2780 (CH$_3$, CH$_2$); 1720 (CO); 1470 (CH$_2$); 1050 (CO).

NMR (CD$_3$OD), δ: 0.70 (s, 3H, 18—CH$_3$); 0.96 (s, 3H, 19—CH$_3$); 1.15 (d, 3H, 23α—CH$_3$); 3.23–3.73 (m, 2H, 3β—CH and 7α—CH); 4.76 (m, 3H, 3α—OH, 7β—OH, 24—COOH). The B-isomer (a white powder m.p. 205° C.) was identified as 23β-methyl-ursodeoxycholic acid (=3α,7β-dihydroxy-23β-methyl-5β-cholan-24-oic acid):

IR (Nujol), cm$^{-1}$: 3580–3210 (OH); 3110–2780 (CH$_3$, CH$_2$); 1720 (CO); 1470 (CH$_2$); 1050 (CO).

NMR (CD$_3$OD),: 0.75 (s, 3H, 18—CH$_3$); 0.96 (s, 3H, 19—CH$_3$); 1.06 (d, 3H, 23β—CH$_3$); 3.33–3.66 (m, 2H, 3β—CH and 7α—CH); 4.75 (m, 3H, 3α—OH, 7β—OH, 24—COOH).

EXAMPLE 2

Sodium tauro-3α,7β-dihydroxy-23-methyl-5β-cholan-24-ate

N-Ethoxycarbonyl-2-ethoxy-1,2-dihydroquinoline (EEDP) (0.5 g) dissolved in 95% ethanol (20 ml) and taurine (0.18 g) dissolved in sodium hydroxide 0.5N (2.87 ml) were added to a solution of 3α,7β-dihydroxy-23-methyl-5β-cholanoic acid (0.58 g) in 95% ethanol (30 ml).

The reaction mixture was stirred at the temperature of 40° C. After 18 hours the solvent was evaporated under vacuum at the temperature of 38° C. and the residue was dissolved in methanol (20 ml). By addition of diethyl ether (80 ml) a suspension was obtained, and it was subsequently centrifuged; the supernatant liquor was decanted and the precipitate was dissolved for three times in methanol (15 ml), precipitated again with ether and centrifuged. The residue thus obtained was dried to 120° (1 mm Hg) for 12 hours in order to give 0.8 g (73%) of sodium 23-methyl-taurodesoxycholate. M.p. 190°–200° C.

IR (Nujol), cm$^{-1}$: 3440 (OH), 1650 (CO).

NMR (CD$_3$OD+D$_2$O+CDCl$_3$), δ: 0.7 (s, 3H, 18—CH$_3$); 0.93 (s, 6H, 19—CH$_3$ and 23—CH$_3$); 2.97 (t, 2H, CH$_2$SO$_3^-$); 3.3–3.6 (m, 2H, CONHCH$_2$); 4.1–4.7 (br m, 5H, 3—CHOH, 7—CHOH, NH).

EXAMPLE 3

(a) 3α,7β-diethoxycarbonyl-12α-hydroxy-23-methyl-5β-cholan-24-oic acid, methyl ester To a solution of N-cyclohexyl-isopropyl-amine (2.8 ml; 0.017 mol) in anhydrous THF (120 ml), 11.4 ml (0.016 mol) of a butyllithium solution were added in 30'; the stirred mixture was then cooled (under nitrogen) to −78° C., and 3α,7β-diethoxycarbonyl-12α-hydroxy-5β-cholan-24-oic acid, methyl ester (2.5 g; 0.0045 mol), dissolved in 22 ml of anhydrous THF was added very slowly (45').

Fifteen minutes after the addition, CH$_3$I (10.2 g; 0.072 mol) was added, and the mixture was brought to room temperature.

After 5 hours the reaction was complete; the solution was acidified with a 10% aqueous solution of HCl and extracted with CHCl$_3$ (3×80 ml). The chloroform solution was washed with water, dried on Na$_2$SO$_4$, and evaporated to dryness. The yield is almost quantitative.

(b) 3α,7β,12α-Trihydroxy-23-methyl-5β-cholan-24-oic acid

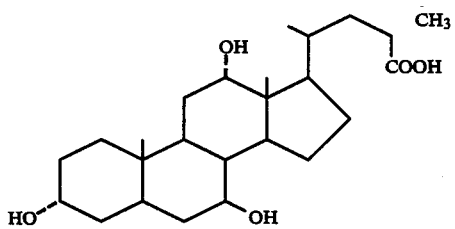

The solution of 3α,7β-diethoxycarbonyl-12α-hydroxy-23-methyl-5β-cholan-24-oic acid, methyl ester (0.6 g; 0.0011 mol) in 20 ml of a water/ethanol mixture (40/60) and 3 g of NaOH was refluxed for 12 hours, then treated with 80 ml of water, acidified with concentrated HCl and extracted with 4×40 ml of CHCl$_3$. The organic solution was washed with NaCl-saturated water and dried on MgSO$_4$. By chromatography on silica gel, under N$_2$-pressure (eluent: CHCl$_3$), 340 mg of the title compound were obtained. M.p. 151°–153° C. The structure of the compound is fully confirmed by the analytical and spectral data.

(c) A-isomer and B-isomer of 3α,7β,12α-trihydroxy-23-methyl-5β-cholan-24-oic acid 1.4 Grams of the acid obtained is part (b) of this Example were chromatographed on a column (h: 30 cm, d: 4.5 cm) of silica gel, under nitrogen pressure, using petroleum ether/diethyl ether 7/3 as eluent. A first crop (600 mg, yield 24%) of an A-isomer was obtained, then a second one (300 mg, yield 55%) of a mixture of A- and B-isomer, and finally a fraction (500 mg, yield 20%) of B-isomer were obtained.

The A-isomer melts at 190°–193° C.

NMR (CD$_3$OD+CDCl$_3$), δ: 0.70 (s, 3H, 18—CH$_3$); 0.95 (s, 3H, 19—CH$_3$); 1.14 (d, 3H, 23—CH$_3$); 3.26–3.67 (2H, br m, 3β—CH and 7α—CH); 3.92 (1H, br m, 12β—CH).

The B-isomer melts at 186°–88° C.

NMR (CD$_3$OD+CDCl$_3$), δ: 0.73 (s, 3H, 18—CH$_3$), 0.95 (s, 3H, 19—CH$_3$), 1.06 (d, 3H, 23—CH$_3$), 3.20–3.60 (br m, 2H, 3β—CH and 7α—CH), 3.90 (br m, 1H, 12β—CH).

The mixture A+B melts at 140°–150° C.

EXAMPLE 4

(a) 3α,7β-diethoxycarbonyl-22-methyl-24-nor-5β-cholan-23-oic acid

To a solution of 6 ml of cyclohexylamine in 20 ml of THF, kept under stirring and N$_2$, 24 ml of a solution of n-butyllithium (0.016 mol), were added (in 20'). After 15 minutes the solution was cooled to −78° C. and slowly treated with 3.9 grams of 3α,7β-diethoxycarbonyl-24-nor-5β-cholan-23-oic acid, methyl ester in 20 ml of THF.

After 15', 20.9 g of CH$_3$I were slowly added; the mixture was then brought to room temperature, stirred for 12 hours, then poured in 100 ml of water and extracted with 3×50 ml of CHCl$_3$. The chloroformic solution was washed with 3×15 ml of HCl 2N, then with water to neutrality. After drying on Na$_2$SO$_4$ the solvent was evaporated to give 5.5 g of a raw product which was eluted on silica gel with petrol ether/diethyl ether 9/1. 2.8 Grams of the pure title compound were obtained.

IR (Nujol), cm$^{-1}$: 1730 (CO).

NRM (CDCl$_3$), δ: 0.68; 0.93; 1.13; 2.0; 3.6; 4.67.

(b)
3α,7β-Dihydroxy-22-methyl-24-nor-5β-cholan-23-oic acid

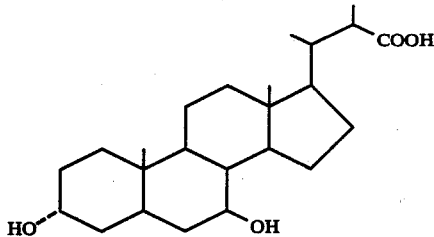

The solution of 1 g of 3α,7β-diethoxycarbonyl-23-methyl-24-nor-5β-cholan-23-oic acid, methyl ester, in 100 ml of a 10% methanolic solution of potassium hydroxyde was refluxed under stirring for 12 hours, then poured in 100 ml of water. The aqueous solution was washed with 2×50 ml of diethyl ether, then acidified with 10% HCl and newly extracted with 3×60 ml of ethyl acetate. The organic solution was dried on $Na_2SO_4$ and the solvent was evaporated to give 0.9 g of a raw product which was eluted on a silica gel column, using petroleum ether/ethyl acetate 7/3: 380 mg of the pure title compound were obtained, m.p. 109°–112° C. The structure is confirmed by the IR and NMR spectra.

The present invention also covers all the industrial aspects connected with the therapeutical use of the compounds of formula (I). Thus, an essential aspect of the invention includes the pharmaceutical formulations containing predetermined amounts of said compounds.

The compounds according to the invention may be administered by oral route or by parenteral route, for instance in the form of tablets, capsules, small envelopes, containing hydrodispersable powders, etc. and vials for injection.

We claim:

1. Compounds of formula I

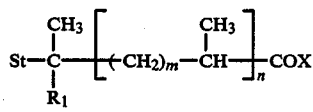
(I)

wherein:

St represents a 17-ethiocholanyl group, having two or the hydroxy groups both in the α and β conformation, some of which may be replaced by keto groups; m and n are zero or 1;
when n is 1, $R_1$ is hydrogen, whereas when n is zero, $R_1$ is methyl;
X represents hydroxy, $OR_3$ (where $R_3$ is a pharmaceutically acceptable cation), taurine or glycine groups of formula —$NH(CH_2)_2SO_3H$ and —NH—$CH_2$—COOH, which may be salified, and stereoisomers thereof.

2. 3α,7β-Dihydroxy-23-methyl-5β-cholan-24-oic acid, its 23α- and 23β-isomers, and pharmaceutically acceptable salts thereof.

3. Tauro-3α,7β-dihydroxy-23-methyl-5β-cholan-24-oic acid, its 22α- and 22β-isomers, and pharmaceutically acceptable salts thereof.

4. 3α,7β,12α-Trihydroxy-23-methyl-5β-cholan-24-oic acid, its 23α- and 23β-isomers, and pharmaceutically acceptable salts thereof.

5. 3α,7β-Dihydroxy-22-methyl-24-nor-5β-cholan-23-oic acid, its 22α- and 22β-isomers, and pharmaceutically acceptable salts thereof.

6. A pharmaceutical composition comprising an effective amount of the compound of claim 1 for treating hepatobiliary functional disorders.

7. A pharmaceutical composition comprising an effective amount of the compound of claim 2 for treating hepatobiliary functional disorders.

8. A pharmaceutical composition comprising an effective amount of the compound of claim 3 for treating hepatobiliary functional disorders.

9. A pharmaceutical composition comprising an effective amount of the compound of claim 4 for treating hepatobiliary functional disorders.

10. A pharmaceutical composition comprising an effective amount of the compound of claim 5 for treating hepatobiliary functional disorders.

11. The pharmaceutical compositions according to claim 6, in the form of capsules, tablets, sugar-coated tablets, syrups, granules, monodose sachets, and vials for injection.

12. A method for treating hepatobiliary functional disorders which comprises administering to a patient a therapeutically effective amount of the compound of claim 1.

13. The method of claim 12, wherein the compound is administered in an amount of 250 to 500 mg/day.

14. The method of claim 12, wherein the compound is orally administered.

15. A method for treating cholesterol gallstones which comprises administering to a patient a therapeutically effective amount of the compound of claim 1.

* * * * *